United States Patent
Ohri et al.

(10) Patent No.: US 9,814,844 B2
(45) Date of Patent: Nov. 14, 2017

(54) DRUG-DELIVERY CANNULA ASSEMBLY

(71) Applicant: COVIDIEN LP, Mansfield, MA (US)

(72) Inventors: Rachit Ohri, Framingham, MA (US); Lan Pham, Nashua, NH (US); Phillip D. Blaskovich, Salem, MA (US); Les Hull, Attleboro, MA (US); Rupal Ayer, Boulder, CO (US); Stephen H. Wu, Chesterfield, MO (US); Clifford J. Herman, Saint Louis, MO (US); William H. Nau, Jr., Longmont, CO (US); Francesca Rossetto, Longmont, CO (US); Allison Waller, Blackstone, MA (US); Wenxing Huang, Shanghai (CN); Paul DiCarlo, Middleboro, MA (US); Mantao Xu, Shanghai (CN); Xingyan Lu, Shanghai (CN); Jiagui Li, Shanghai (CN); Qinlin Gu, Shanghai (CN); Harold M. Martins, Newton, MA (US)

(73) Assignee: COVIDIEN LP, Mansfield, MA (US)

( * ) Notice: Subject to any disclaimer, the term of this patent is extended or adjusted under 35 U.S.C. 154(b) by 209 days.

(21) Appl. No.: 14/011,414

(22) Filed: Aug. 27, 2013

(65) Prior Publication Data
US 2015/0065964 A1 Mar. 5, 2015

(51) Int. Cl.
*A61M 5/32* (2006.01)
*A61B 17/34* (2006.01)
(Continued)

(52) U.S. Cl.
CPC ......... *A61M 5/329* (2013.01); *A61B 17/3421* (2013.01); *A61B 18/1477* (2013.01);
(Continued)

(58) Field of Classification Search
CPC .... A61M 5/32; A61M 5/3295; A61M 5/3298; A61M 5/343; A61B 18/14; A61B 2018/143; A61B 18/1442
See application file for complete search history.

(56) References Cited

U.S. PATENT DOCUMENTS

D223,367 S 4/1972 Kountz
D263,020 S 2/1982 Rau, III
(Continued)

FOREIGN PATENT DOCUMENTS

CN 1103807 A 6/1995
DE 390937 C 3/1924
(Continued)

OTHER PUBLICATIONS

U.S. Appl. No. 13/419,981, filed Mar. 14, 2012, Joseph D. Brannan.
(Continued)

*Primary Examiner* — Imani Hayman
*Assistant Examiner* — Nilay Shah (57) ABSTRACT

A drug-delivery cannula assembly includes a cannula housing adapted for receiving at least one obturator shaft of an obturator assembly therethrough, one or more cannulae, and a supply line coupled to the cannula housing. The cannula housing is adapted for receiving one or more obturator shafts of an obturator assembly therethrough. The one or more cannulae define a longitudinal axis and a passageway aligned with the longitudinal axis. The one or more cannulae each include a proximal end coupled to the cannula housing. The cannula housing is configured to fluidly-couple the one or more cannulae to a source of a drug delivery supply for supplying drugs via the supply line to the one or more cannulae.

5 Claims, 8 Drawing Sheets

(51) Int. Cl.
*A61B 18/14* (2006.01)
*A61M 25/00* (2006.01)
*A61B 18/00* (2006.01)

(52) U.S. Cl.
CPC ..... *A61B 18/1487* (2013.01); *A61M 25/0097* (2013.01); *A61B 17/3478* (2013.01); *A61B 2017/3447* (2013.01); *A61B 2018/00577* (2013.01); *A61B 2018/143* (2013.01); *A61B 2218/002* (2013.01); *A61M 25/00* (2013.01); *A61M 2025/0037* (2013.01); *A61M 2202/0007* (2013.01)

(56) References Cited

U.S. PATENT DOCUMENTS

| | | | |
|---|---|---|---|
| D266,842 S | 11/1982 | Villers et al. | |
| 4,430,081 A * | 2/1984 | Timmermans | 604/256 |
| D278,306 S | 4/1985 | McIntosh | |
| D295,893 S | 5/1988 | Sharkany et al. | |
| D295,894 S | 5/1988 | Sharkany et al. | |
| 5,041,098 A * | 8/1991 | Loiterman | A61M 39/0208 604/175 |
| 5,356,381 A * | 10/1994 | Ensminger | A61M 39/0208 604/181 |
| D354,218 S | 1/1995 | Van de Peer | |
| 5,403,311 A | 4/1995 | Abele et al. | |
| 5,472,441 A | 12/1995 | Edwards et al. | |
| 5,921,982 A | 7/1999 | Lesh et al. | |
| 6,016,452 A | 1/2000 | Kasevich | |
| D424,693 S | 5/2000 | Pruter | |
| D424,694 S | 5/2000 | Tetzlaff et al. | |
| D425,201 S | 5/2000 | Tetzlaff et al. | |
| 6,176,856 B1 | 1/2001 | Jandak et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,402,742 B1 | 6/2002 | Blewett et al. | |
| 6,477,426 B1 | 11/2002 | Fenn et al. | |
| 6,478,793 B1 | 11/2002 | Cosman et al. | |
| 6,673,070 B2 | 1/2004 | Edwards et al. | |
| D487,039 S | 2/2004 | Webster et al. | |
| 6,788,977 B2 | 9/2004 | Fenn et al. | |
| D496,997 S | 10/2004 | Dycus et al. | |
| D499,181 S | 11/2004 | Dycus et al. | |
| 7,025,765 B2 | 4/2006 | Balbierz et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,160,296 B2 * | 1/2007 | Pearson | A61B 18/1477 606/42 |
| D541,418 S | 4/2007 | Schechter et al. | |
| D541,938 S | 5/2007 | Kerr et al | |
| D564,662 S | 3/2008 | Moses et al. | |
| 7,393,352 B2 | 7/2008 | Berube | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,842,076 B2 | 11/2010 | Zikorus et al. | |
| D634,010 S | 3/2011 | DeCarlo | |
| 7,918,852 B2 | 4/2011 | Tullis et al. | |
| 8,172,757 B2 | 5/2012 | Jaffe et al. | |
| D681,810 S | 5/2013 | DeCarlo | |
| 2002/0120260 A1 | 8/2002 | Morris et al. | |
| 2004/0030250 A1* | 2/2004 | Stewart | 600/439 |
| 2004/0267256 A1* | 12/2004 | Garabedian et al. | 606/41 |
| 2006/0041243 A1 | 2/2006 | Nayak et al. | |
| 2006/0241576 A1 | 10/2006 | Diederich et al. | |
| 2007/0073248 A1 | 3/2007 | Moenning | |
| 2007/0161958 A1* | 7/2007 | Glenn | A61M 39/0208 604/175 |
| 2007/0244529 A1 | 10/2007 | Choi et al. | |
| 2007/0270710 A1* | 11/2007 | Frass et al. | 600/567 |
| 2007/0270789 A1 | 11/2007 | Berger | |
| 2007/0287996 A1 | 12/2007 | Rioux | |
| 2009/0149850 A1 | 6/2009 | Turovskiy et al. | |
| 2010/0056989 A1* | 3/2010 | McKay | 604/28 |
| 2010/0125269 A1 | 5/2010 | Emmons et al. | |
| 2011/0077644 A1 | 3/2011 | Pham et al. | |
| 2013/0085487 A1 | 4/2013 | Temelli et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |

(56) References Cited

FOREIGN PATENT DOCUMENTS

| JP | 08252263 A | 10/1996 |
|---|---|---|
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 95/22285 A1 | 8/1995 |
| WO | 9904710 A1 | 2/1999 |
| WO | WO00/12010 | 3/2000 |
| WO | 00/36985 A2 | 6/2000 |
| WO | 01/08573 A2 | 2/2001 |
| WO | WO01/74252 | 10/2001 |
| WO | WO2006/105121 | 10/2006 |
| WO | WO2006/138719 | 12/2006 |
| WO | WO2008/144341 | 11/2008 |
| WO | WO2009/065058 | 5/2009 |
| WO | 2010/035831 A1 | 4/2010 |

OTHER PUBLICATIONS

U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
European Search Report dated Sep. 26, 2013 for EP 13 17 0016.
U.S. Appl. No. 08/136,098, filed Oct. 14, 1993; Roger A. Stern.
U.S. Appl. No. 08/483,742, filed Jun. 7, 1995; Roger A. Stern.

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold: 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.

(56) References Cited

OTHER PUBLICATIONS

Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002
LigaSureTM Vessel Sealing System, the Seal of Confidence in General , Gynecologic, Urologic, and Laparoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P. R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.

(56) References Cited

OTHER PUBLICATIONS

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Longterm Results in 117 Patients", Radiology, vol. 221, pp. 159-166.

Solbiati et al. (1995) "Percutaneous US-guided RF Tissue Ablation of Liver Metastases: Long-term Follow-up", Radiology, pp. 195-203.

Stagegaard, N., Petersen H.H., Chen X., Svendsen J.H., "Indication of the Radiofrequency Induced Lesion Size by Pre-ablation Measurements" Europace (2005) 7, 525-534.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

Urologix, Inc.—Medical Professionals: TargisTM Technology (Date Unknown). "Overcoming the Challenge" located at: <http://www.urologix.comlmedicaUtechnology.html > Nov. 18, 1999; 3 pages.

Urrutia et al., (1988). "Retractable-Barb Needle for Breast Lesion Localization: Use in 60 Cases," Radiology 169 (3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation—'COA-COMP'" Neurosurgical Review 7:2-3 (1984) pp. 187-190.

W. Scott Helton, "LigaSureTM Vessel Sealing System: Revolutionary Hemostasis Product for General Surgery" Sales/ Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.

European Search Report for EP 14173860 dated Mar. 9, 2015.

\* cited by examiner

DRUG-DELIVERY CANNULA ASSEMBLY

BACKGROUND

1. Technical Field

The present disclosure relates to electrosurgical systems and devices for performing medical procedures. The present disclosure relates to the administration of beneficial agents in general, which include any physiologically, pharmacologically active and/or psychotropic substance(s). More particularly, the present disclosure relates to a drug-delivery cannula assembly suitable for use with medical devices, such as for example, electrosurgical devices, and electrosurgical systems including the same.

2. Discussion of Related Art

Surgical techniques and instruments have been developed that allow the surgeon to perform an increasing range of surgical procedures with minimal incisions into the skin and body tissue of the patient. Minimally invasive surgery has become widely accepted in many medical specialties, often replacing traditional open surgery. Minimally invasive surgical procedures where trocar assemblies are desirable or even necessary are continually increasing in number and variety.

Minimally-invasive surgical procedures are performed throughout the body and generally rely on obtaining access to an internal surgical site through a relatively small pathway, often less than one centimeter in diameter, to the surgical site. One method of providing such a pathway is by inserting a cannula and trocar assembly through the skin of the patient. Commonly, to place the trocar-cannula, the penetrating tip of the obturator of the trocar is pushed through the skin and underlying tissue until the distal end of the cannula is within the body cavity. Alternatively, some trocar devices have a blunt obturator for placing the cannula through a previously-made incision. Once the trocar has been properly positioned, the obturator is removed and the cannula is then available as a pathway between the surgical site and the exterior of the patient's body through which the surgeon may introduce the various surgical instruments required to perform the desired procedures. Surgical instruments insertable through a cannula include forceps, clamps, scissors, probes, flexible or rigid scopes, staplers and cutting instruments.

The term "trocar" originally referred to a pointed device for penetrating body tissues having a three-faceted pyramidal point. Commonly, a trocar includes an obturator assembly including a shaft having a proximal end connected to a hand grip and a sharpened, pyramidal or conical tip at the distal end of the shaft for penetrating body tissue. Trocars may have their obturators secured to the hand grip so that the obturator cannot rotate separately from the hand grip. Some obturators include a tip portion that is detachable and disposable.

"Trocar" is a term now widely used to describe surgical instruments for placing an access cannula into a body cavity for endoscopic surgery, including laparoscopy, arthroscopy and thoracoscopy. This type of trocar device includes a trocar cannula, also referred to as a trocar tube or sleeve, with an obturator assembly removeably inserted through the lumen of the cannula for penetrating the body tissue.

Trocar assemblies are typically made of metal to facilitate sterilization and re-use. Medical grade stainless steel and titanium metal are commonly used.

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

The benefits provided by controlled delivery of active agents for the treatment of injury or disease are well recognized in the art and various approaches have been taken to realize the goal of delivering active agents at desired rates over predetermined periods of time. Various different implantable controlled delivery formulations are known in the art, and various different mechanisms have been employed for delivering an active agent from implantable formulations at a controlled rate over time.

Medical imaging has become a significant component in the clinical setting and in basic physiology and biology research, e.g., due to enhanced spatial resolution, accuracy and contrast mechanisms that have been made widely available. Medical imaging now incorporates a wide variety of modalities, e.g., computed tomography (CT) and magnetic resonance imaging (MRI), which noninvasively capture the structure and/or function of the human body. Such images are acquired and used in many different ways including medical images for diagnosis, staging and therapeutic management of malignant disease.

Medical image processing, analysis and visualization play an increasingly useful role in disease diagnosis and monitoring as well as, among other things, surgical planning and monitoring of therapeutic procedures. A contrast agent may be used for enhancement of the contrast of structures or fluids within the body (or region of interest) in medical imaging to allow visualization and evaluation of lesions seen minimally, if at all, with imaging alone. There is a continuing need for devices capable of dispensing a contrast agent to enhance the visualization of the lesion during a surgical procedure.

Despite advancements in the use of electrosurgical devices for treating biological tissue, there are still concerns for tumor reoccurrence. A further continuing need exists for devices capable of dispensing a controlled delivery formulation of a desired active agent, which may help reduce or eliminate tumor reoccurrence.

SUMMARY

There is a need for drug-delivery devices suitable for use with surgical instruments, e.g., ablation devices, to provide the capability of dispensing a controlled delivery formulation of a desired active agent (and/or contrast agent). The combination of ablation (e.g., RF ablation and/or microwave ablation) and drug delivery may help to reduce or eliminate tumor reoccurrence. The combination of ablation and contrast agent introduction may help to enhance the visualization of the lesion during the treatment procedure. There is a need for drug-delivery devices configured for use with ablation devices to provide the capability of dispensing an active agent in a controlled delivery formulation and/or non-active agent (e.g., contrast agent) before, during and/or after ablation, e.g., without the need for further manipulation of the device.

As it is used in this description, "ablation procedure" generally refers to any ablation procedure, such as, for example, microwave ablation, radio frequency (RF) ablation or microwave ablation-assisted resection. As it is used in this description, "energy-delivery device" generally refers to any device that can be used to transfer energy from a power generating source, such as a microwave or RF electrosurgical generator, to tissue. For the purposes herein, the term "ablation device" is interchangeable with the term "energy-delivery device." As it is used in this description, "transmission line" generally refers to any transmission medium that can be used for the propagation of signals from one point to another.

As it is used in this description, "trocar" generally includes sharp-pointed surgical instruments used to penetrate body tissue, although the instruments may not have a three-faced pyramidal tip from which the term "trocar" is derived. As it is used in this description, "frusto-conical" refers to a geometric form based on a cone of which the apex has been "cut off" by a plane parallel to its base.

For the purposes of this description, the terms "drug," "drug agent," "implantable drug agent," "active agent," "beneficial agent," "therapeutic agent," "therapeutic molecule," and the like are used interchangeably herein, and may include, for example, small molecules, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species. Some examples of drug agents that may be delivered by devices according to embodiments of the present disclosure are provided later in this description.

According to an aspect of the present disclosure, a drug-delivery device is provided. The drug-delivery cannula assembly includes a cannula housing adapted for receiving one or more obturator shafts of an obturator assembly therethrough, one or more cannulae, and a supply line coupled to the cannula housing. The one or more cannulae define a longitudinal axis and a passageway aligned with the longitudinal axis. The one or more cannulae each include a proximal end coupled to the cannula housing. The cannula housing is configured to fluidly-couple the one or more cannulae to a source of a drug delivery supply for supplying drugs via the supply line to the one or more cannulae.

According to an aspect of the present disclosure, a drug-delivery device is provided. The drug-delivery cannula assembly includes a cannula housing adapted for receiving one or more ablation probes of an ablation device therethrough, one or more cannulae, and a supply line coupled to the cannula housing. The one or more cannulae define a longitudinal axis and a passageway aligned with the longitudinal axis. The one or more cannulae each include a proximal end coupled to the cannula housing. The cannula housing is configured to fluidly-couple the one or more cannulae to a source of a drug delivery supply for supplying drugs via the supply line to the one or more cannulae.

BRIEF DESCRIPTION OF THE DRAWINGS

Objects and features of the presently-disclosed drug-delivery cannula assemblies suitable for use with electro-surgical devices, e.g., ablation devices, and electrosurgical systems including the same will become apparent to those of ordinary skill in the art when descriptions of various embodiments thereof are read with reference to the accompanying drawings, of which.

DETAILED DESCRIPTION

Hereinafter, embodiments of the presently-disclosed drug-delivery cannula assembly suitable for use with electrosurgical devices, e.g., ablation devices, and electrosurgical systems including the same are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is farther from the user.

The principles of the present disclosure are applicable to a variety of surgical devices adapted for providing access to a surgical site within a patient's body. These devices include trocar assemblies, access cannulae, catheters, scopes, etc. The presently-disclosed drug-delivery cannula assemblies are contemplated for use in various surgical procedures, e.g., minimally invasive procedures or open surgical procedures. Portions of the presently disclosed drug-delivery cannula assemblies may be disposable, replaceable and/or reusable.

Figure 1:
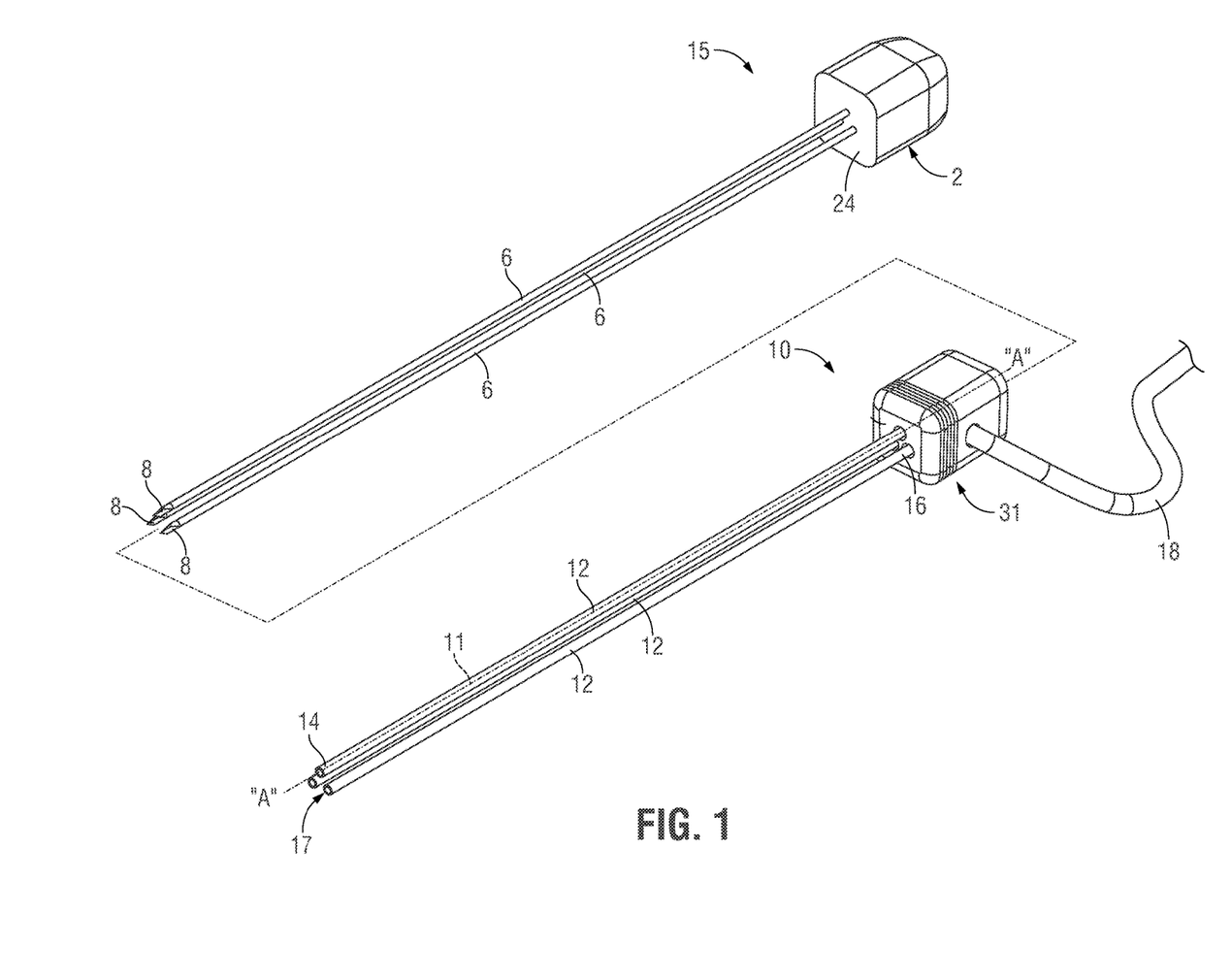
FIG. 1 is a bottom perspective view of an obturator assembly and a drug-delivery cannula assembly, shown separated, the drug-delivery cannula assembly configured to receive the obturator assembly, in accordance with an embodiment of the present disclosure.
Figure 2:
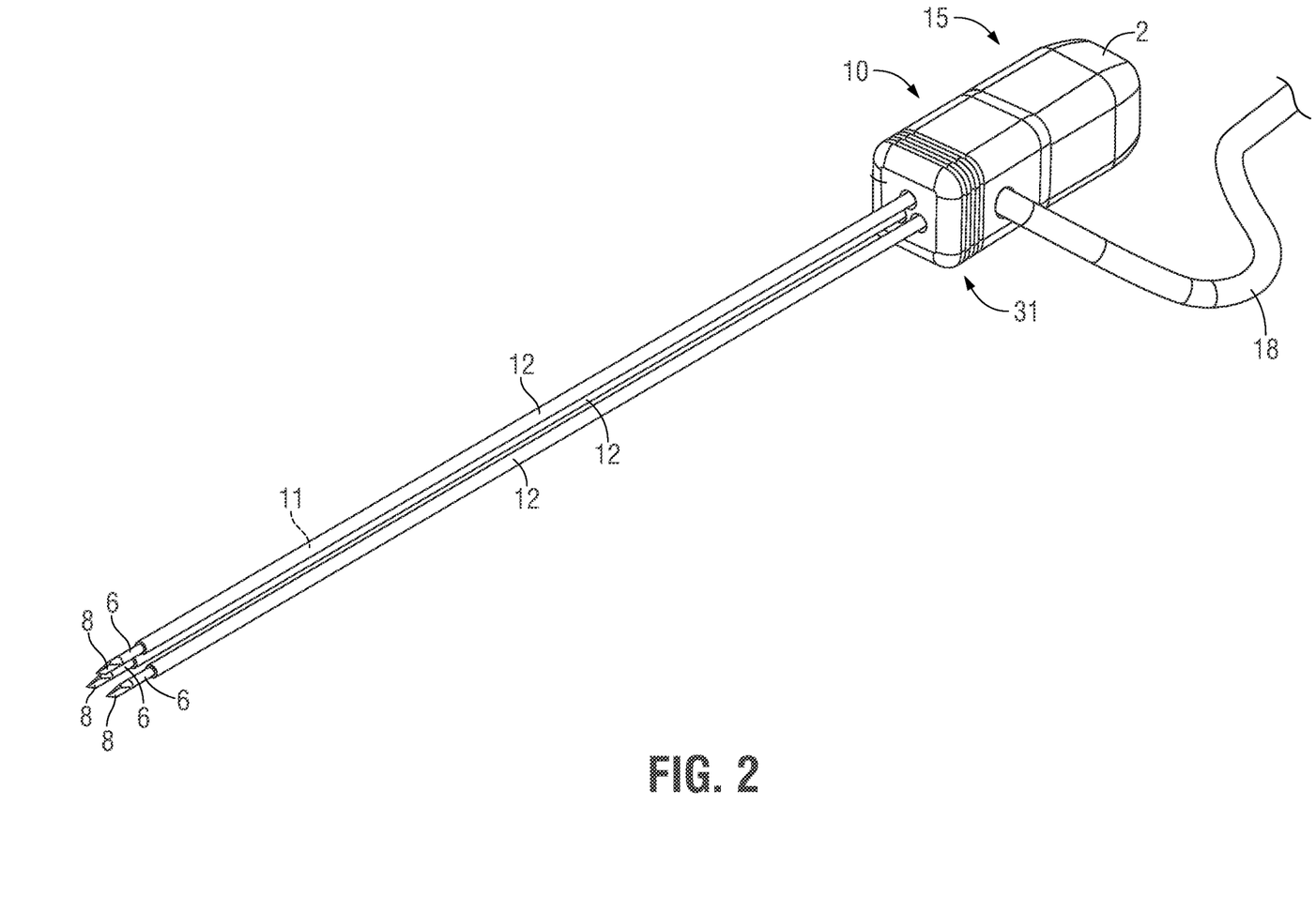
FIG. 2 is a bottom perspective, assembled view of the drug-delivery cannula assembly including the obturator assembly of FIG. 1 in accordance with an embodiment of the present disclosure.

FIGS. 1 and 2 show an obturator assembly 15 and a drug-delivery cannula assembly 10 in accordance with an embodiment of the present disclosure. Drug-delivery cannula assembly 10, which is described in more detail later in this description, generally includes a cannula housing 31 and one or more cannulae 12. Cannula housing 31 may be formed of any suitable material or combination of materials by any suitable process. In some embodiments, as shown in FIGS. 1 through 6, drug-delivery cannula assembly 10 includes three elongated, substantially cylindrically-shaped cannulae 12. In some embodiments, the cannula housing 31 may be adapted to releaseably engage the cannulae 12.

Obturator assembly 15 is adapted to cooperate with the drug-delivery cannula assembly 10. Obturator assembly 15 includes a hand grip 2 configured to be grasped by the user, three obturator shafts 6 connected to the hand grip 2 and having a distal end, which may include a sharpened tip portion. In some embodiments, as shown in FIGS. 1 and 2, a penetrating member 8 is disposed adjacent to the distal end of the obturator shafts 6. Obturator shaft 6 may be formed of any substantially rigid material, such as metal, e.g., medical grade stainless steel or titanium, or any suitable rigid polymeric material. The shape and size of the obturator shaft 6 and the penetrating member 8 may be varied from the configuration depicted in FIGS. 1 and 2.

Hand grip 2 is generally configured to be grasped by the user, and may be provided with a cushioned, slip-resistant member. A cushioned member (not shown) may be formed from a thermoplastic elastomer, e.g., Versaflex™ or Santaprene™, and over-molded onto the hand grip 2 of the obturator assembly 15. Alternatively, a cushioned member may be formed of other cushioned or pliant materials, e.g., elastomeric or synthetic materials, including isoprenes, nitrile or silicon containing material, etc. The cushioned member may be fastened to the hand grip 2 using any suitable fastening techniques, e.g., physical, chemical or mechanical, including adhesives, welding, screws, etc. The shape and size of the hand grip 2 may be varied from the configuration depicted in FIGS. 1 and 2.

In some embodiments, a lower portion 24 of the hand grip 2 of the obturator assembly 15 may be configured for mating engagement with an upper portion 36 (FIG. 6) of the cannula housing 31 of the drug-delivery cannula assembly 10, e.g., to improve stability, enhance safety, and/or provide surgeons with enhanced ease of use. In some embodiments, the lower portion 24 of the hand grip 2 may be configured with one or more pins (not shown) for engaging one or more pin-receiving holes (not shown) in the upper portion 36 (FIG. 6) of the cannula housing 31 for releaseably coupling the obturator assembly 15 and the drug-delivery cannula assembly 10. Additionally, or alternatively, the upper portion 36 of the cannula housing 31, or a portion thereof, and/or the lower portion 24 of the hand grip 2, or a portion thereof, may formed of a magnetic material, e.g., any material capable of producing a magnetic field. Various mechanisms for releaseably coupling the obturator assembly 15 and the drug-delivery cannula assembly 10 may be employed.

Each of the cannulae 12 defines a longitudinal axis "A-A" (FIGS. 1 and 3) and includes an upper (proximal) end 16 defining an inlet opening, a lower (distal) end 14 defining an outlet opening 17, and a passageway 11 of generally tubular shape extending from the inlet opening to the outlet opening 17 along the longitudinal axis "A-A". Passageway 11 is configured to slideably receive the obturator shaft 6 of the obturator assembly 15. Passageway 11 is configured to permit introduction of one or more surgical instruments used in performing a surgical procedure.

In some embodiments, the cannulae 12 may include a converging or frusto-conical section extending from the upper end 16. Cannula housing 31 may be adapted to releaseably engage an outer surface of the converging or frusto-conical section. Additionally, or alternatively, the hand grip 2 of the obturator assembly 15 may include a distal end portion 24 configured to engage an inner surface of the converging or frusto-conical section such that the obturator assembly 15 is releaseably securable thereto.

Cannulae 12 are illustrated in FIGS. 1 through 6, as being of monolithic construction. In alternative embodiments, the cannulae 12 may be formed of multiple components and/or multiple materials. The shape and size of the cannulae 12 may be varied from the configuration depicted in FIGS. 1 through 6. One or more of the cannulae 12 may include a seal "S" mounted adjacent to the upper end 16 thereof. Any suitable seal type may be utilized including septum seals, gel seals, flapper valves, duck-bill seals, etc.

Figure 3:
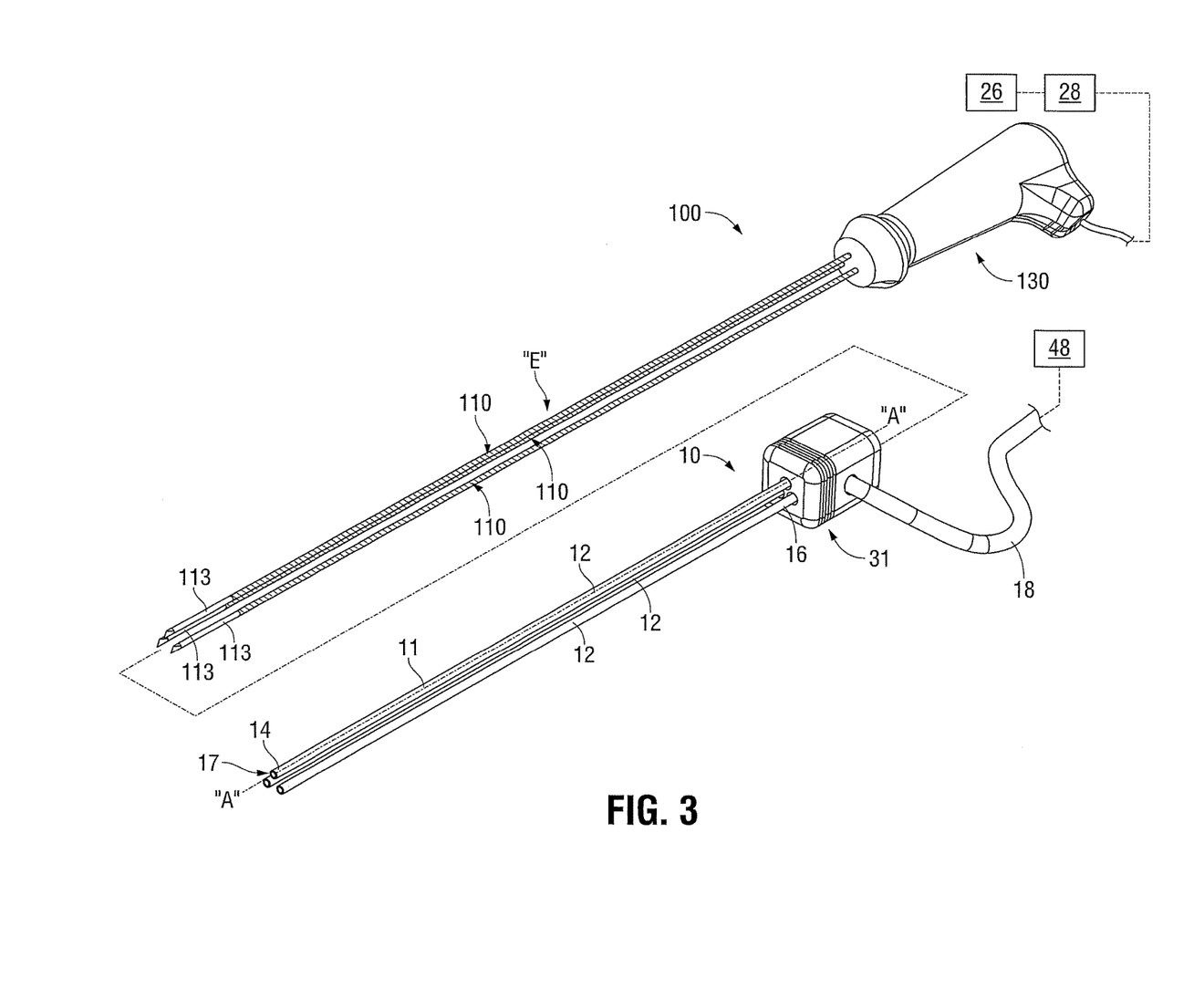
FIG. 3 is a bottom perspective view of an ablation device and a drug-delivery cannula assembly, shown separated, the drug-delivery cannula assembly configured to receive the ablation device, in accordance with an embodiment of the present disclosure.

In FIG. 3, the drug-delivery cannula assembly 10 of FIGS. 1 and 2 is shown with an electrosurgical device 100. Electrosurgical device 100 is operatively connected via a transmission line to an electrosurgical power generating source 28, e.g., a microwave or radio frequency (RF) electrosurgical generator. Power generating source 28 may be any generator suitable for use with electrosurgical devices and may be configured to provide various frequencies of energy. In some embodiments, electrosurgical device 100 (also referred to herein as ablation device 100) is disposed in fluid communication with a coolant source (not shown).

Figure 5:
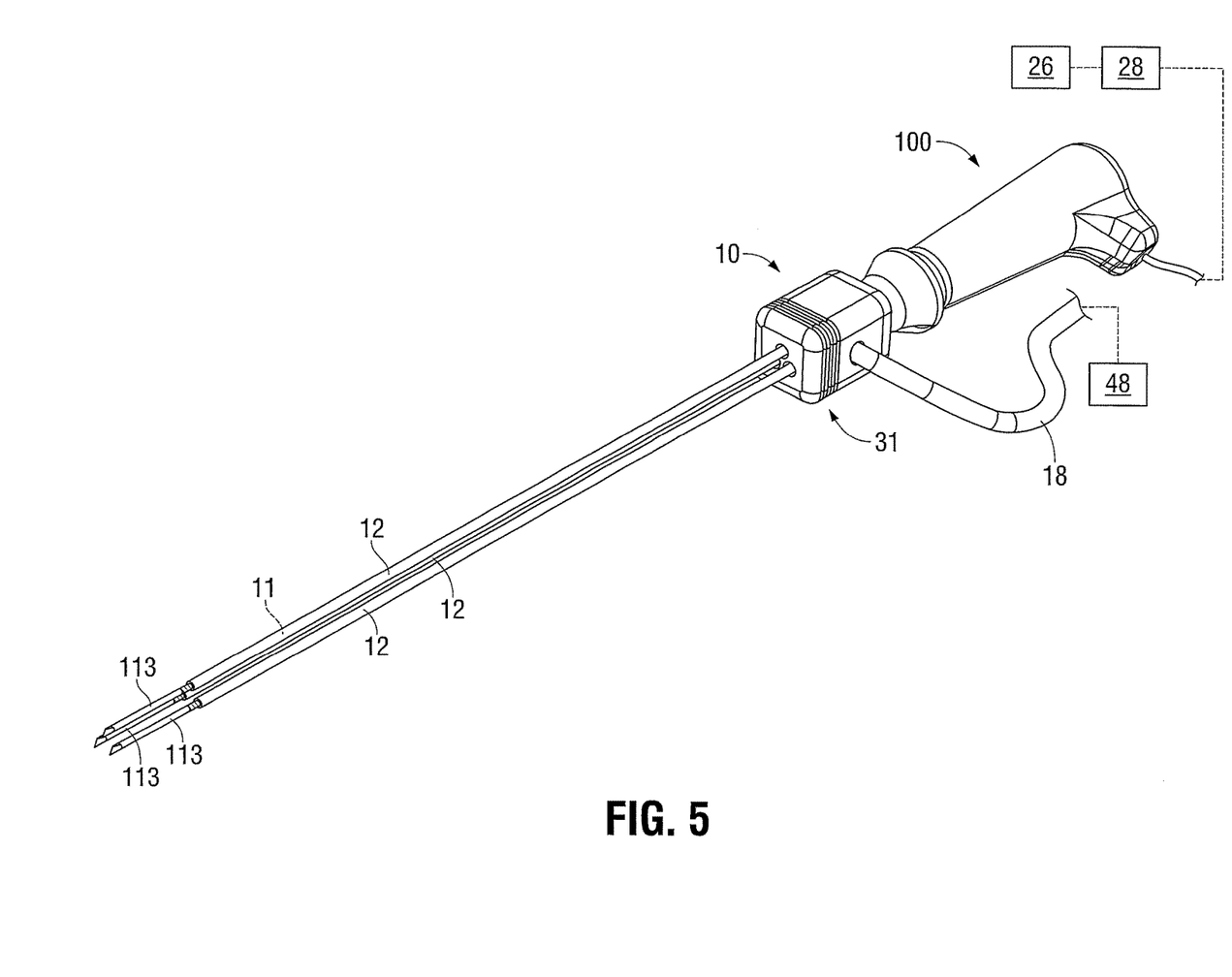
FIG. 5 is a bottom perspective, assembled view of the drug-delivery cannula assembly including the ablation device of FIG. 1 in accordance with an embodiment of the present disclosure.

Ablation device 100 includes an electrode array "E" and a handle assembly 130. Electrode array "E" may include one or more ablation electrodes 110. In some embodiments, as shown in FIG. 3, the electrode array "E" includes three ablation electrodes 110 supported on and/or operatively connected to the handle assembly 130. As shown in FIG. 5, when the ablation device 100 is coupled to the drug-delivery cannula assembly 10, the distal end portion 113 of the ablation electrodes 110 extends distally from the outlet opening 17 of the cannulae 12. The shape, size and number of ablation electrodes 110 of the electrode array "E" may be varied from the configuration depicted in FIG. 3. Ablation device 100 may include additional, fewer, or different components than shown in FIG. 3, depending upon a particular purpose or to achieve a desired result. Examples of ablation device embodiments are shown and described in commonly assigned U.S. patent application Ser. No. 13/834,581, entitled "MICROWAVE ENERGY-DELIVERY DEVICE AND SYSTEM," filed on Mar. 15, 2013, and U.S. Provisional Application Ser. No. 61/783,921, entitled "MICROWAVE ABLATION CATHETER AND METHOD OF UTILIZING THE SAME," filed on Mar. 14, 2013, the disclosures of which are herein incorporated by reference in their entireties.

Figure 4:
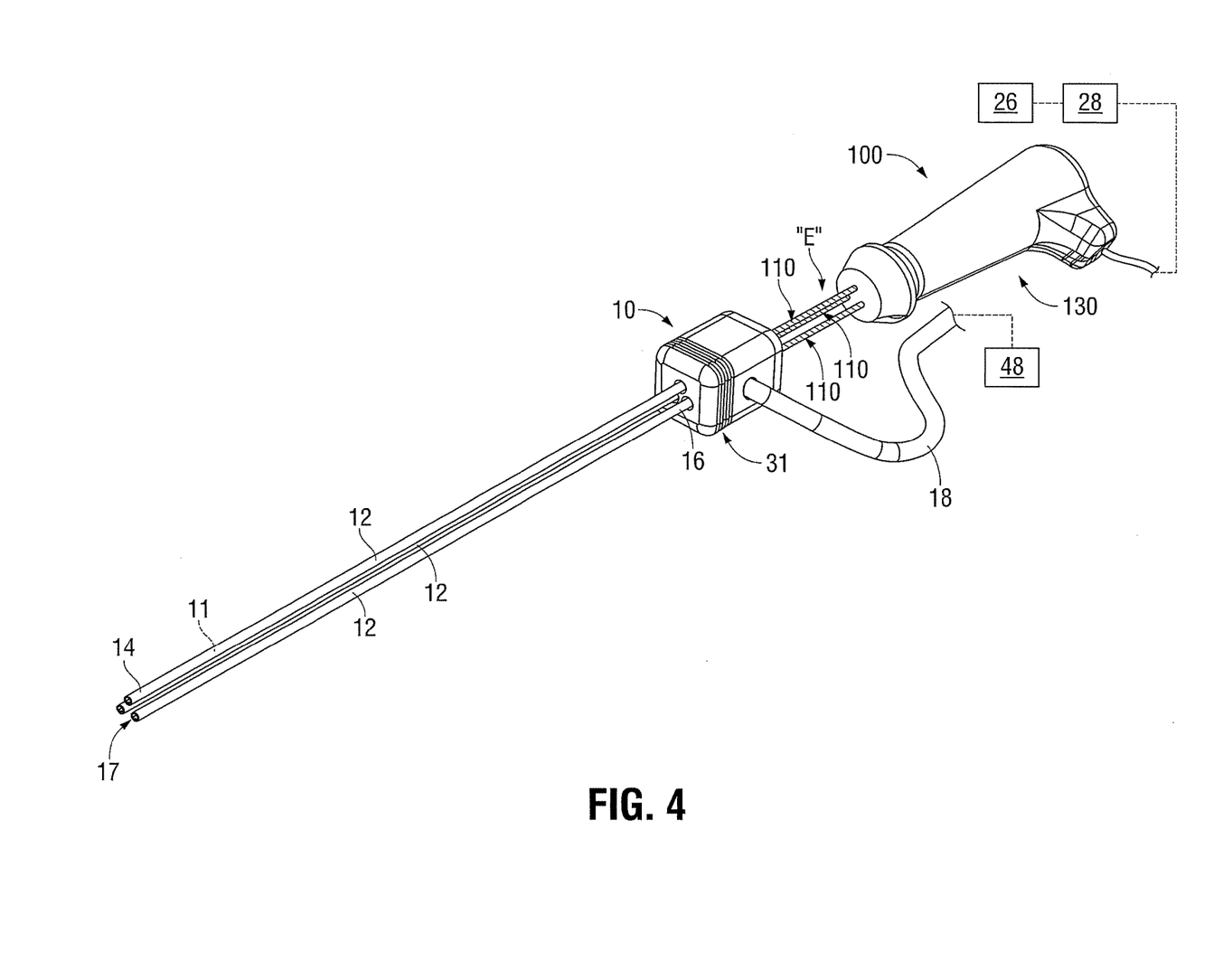
FIG. 4 is a bottom perspective, partially assembled view of the drug-delivery cannula assembly including the ablation device of FIG. 1 in accordance with an embodiment of the present disclosure.

In some embodiments, as shown in FIGS. 3 through 5, a controller 26 is communicatively-coupled to the electrosurgical power generating source 28. Controller 26 may include any type of computing device, computational circuit, or any type of processor or processing circuit capable of executing a series of instructions that are stored in a memory (not shown) associated with the controller 26. Functions of the controller 26 may be integrated with those of the electrosurgical power generating source 28 and/or may be integrated with other electrosurgical system component(s).

As shown in FIGS. 3 through 5, a drug and/or contrast agent supply line 18 is provided to fluidly-couple the drug-delivery cannula assembly 10 to a source of the drug and/or contrast agent delivery supply 48 for supplying drugs and/or contrast agent via the cannula housing 31 to the cannulae 12. A fluid-movement device (not shown) may be fluidly coupled between the source of the drug (and/or contrast agent) and the drug-delivery cannula assembly 10, and the controller 26 may be communicatively-coupled to the fluid-movement device. In some embodiments, the controller 26 may be configured to control operation(s) of the fluid-movement device, e.g., during an ablation procedure based on one or more operating parameters of the electrosurgical power generating source 28.

Figure 6:
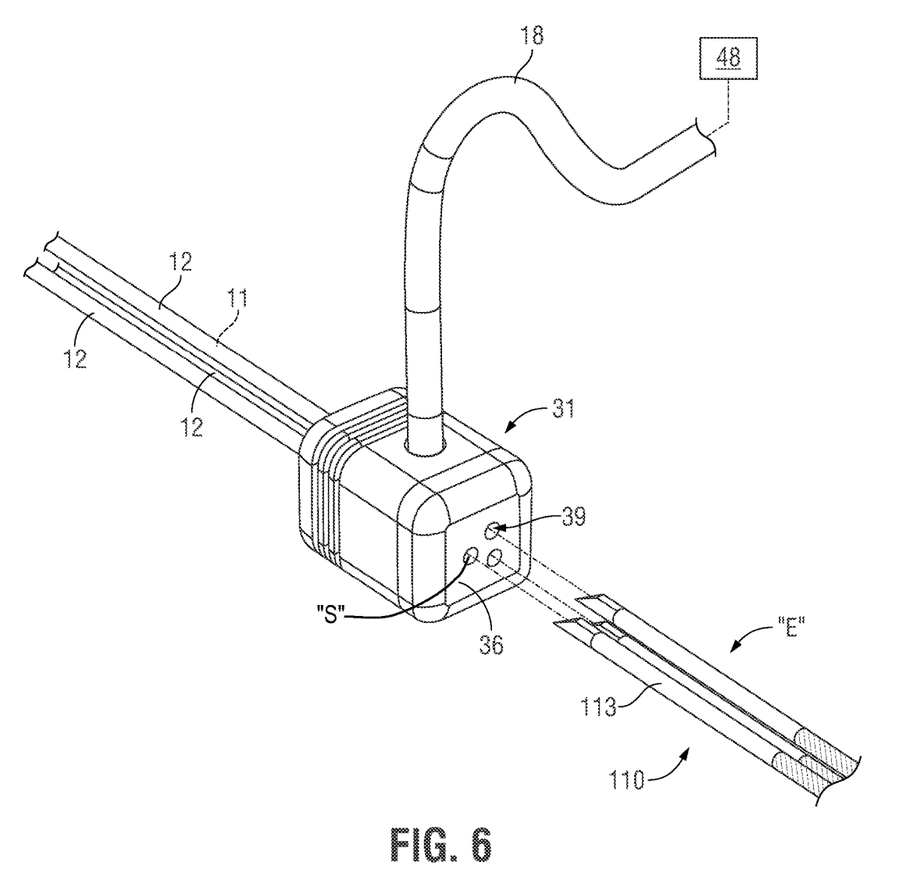
FIG. 6 is top perspective view of the drug-delivery cannula assembly of FIG. 1, shown with a distal end portion of an electrode array of an ablation device, such as the ablation device of FIG. 1, in accordance with an embodiment of the present disclosure.

As shown in FIG. 6, the upper portion 36 of the cannula housing 31 includes three openings 39 defined therein. Each of the openings 39 is configured to receive a penetrating member 8 of an obturator assembly 15 therethrough and configured to receive an ablation electrode 110 of an ablation device 100 therethrough. Cannula housing 31 is configured to support each of the cannulae 12 at a respective opening defined on a lower (distal) portion of the cannula housing 31 such that the upper ends 16 thereof are disposed in fluid communication with the openings 39. In some embodiments, the cannula housing 31 includes an actuator (not shown), such as a slideably moveable member, e.g., thumb-slide actuator, adapted to allow the user to selectively initiate/activate the delivery of drug and/or contrast agent through the drug-delivery cannula assembly 10 to the tissue site.

Figure 7:
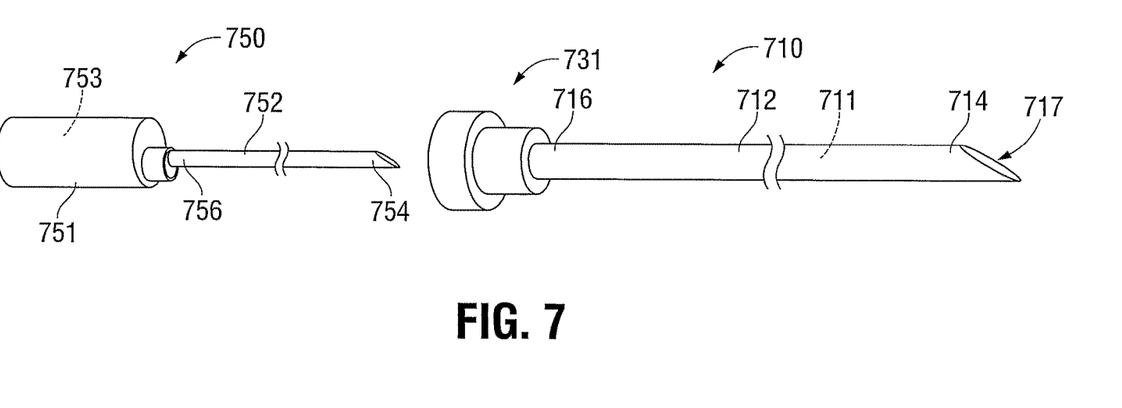
FIG. 7 is perspective view of a drug-delivery device and a cannula assembly, shown separated, the cannula assembly configured to receive the drug-delivery device, in accordance with an embodiment of the present disclosure.

FIG. 7 shows a drug-delivery device 750 and a cannula assembly 710. Cannula assembly 710 is configured to receive the drug-delivery device 750 therethrough. Cannula assembly 710 includes a cannula housing 731 and a cannula 712. Cannula 712 includes an proximal end 716, a distal end 714 defining an outlet opening 717, and a passageway 711 of generally tubular shape extending from the proximal end 716 to the distal end 714.

Drug-delivery device 750 includes a housing member 751 and a delivery needle 752 having a distal end 754 and a proximal end 756 coupled to the housing member 751. Housing member 751 defines a chamber 753 therein. In some embodiments, the chamber 753 is configured to contain an agent for delivery through the delivery needle 752 to tissue (not shown).

Figure 8:
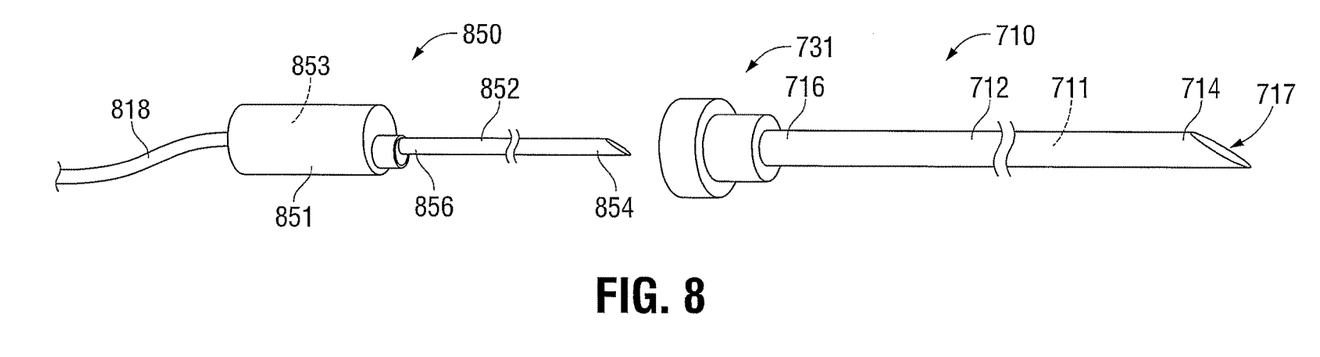
FIG. 8 is perspective view of another embodiment a drug-delivery device and the cannula assembly of FIG. 7, shown separated, with a handle member of the drug-delivery device coupled to a supply line for supplying agents to the drug-delivery device, in accordance with an embodiment of the present disclosure.

FIG. 8 shows a drug-delivery device 850 and the cannula assembly 710 shown in FIG. 7. Drug-delivery device 850 includes a housing member 851 and a delivery needle 852 having a distal end 854 and a proximal end 856 coupled to the housing member 851. Housing member 851 defines a chamber 853 therein. A supply line 818 is coupled to the housing member 851 such that the chamber 853 is disposed in fluid communication with the supply line 818. In some embodiments, the supply line 818 may be coupled to a source of drug and/or contrast agent delivery supply (not shown) for supplying drugs and/or contrast agent via the housing member 851 to the delivery needle 852.

Figure 9:
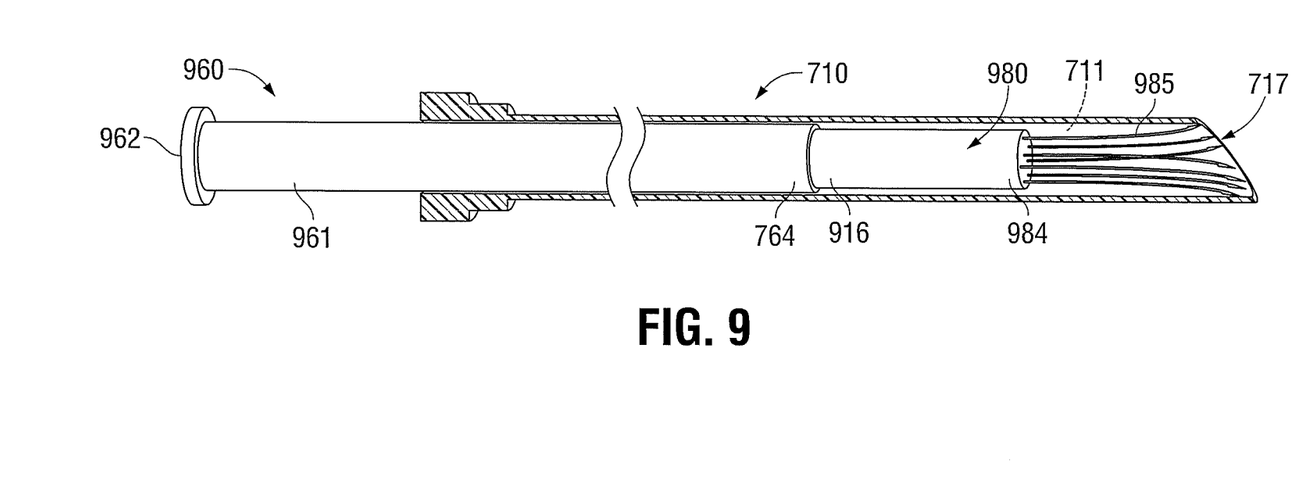
FIG. 9 is cross-sectional view of a drug eluting rod and a pusher rod disposed in association with the cannula assembly of FIG. 7, shown in a first configuration, in accordance with an embodiment of the present disclosure.
Figure 10:
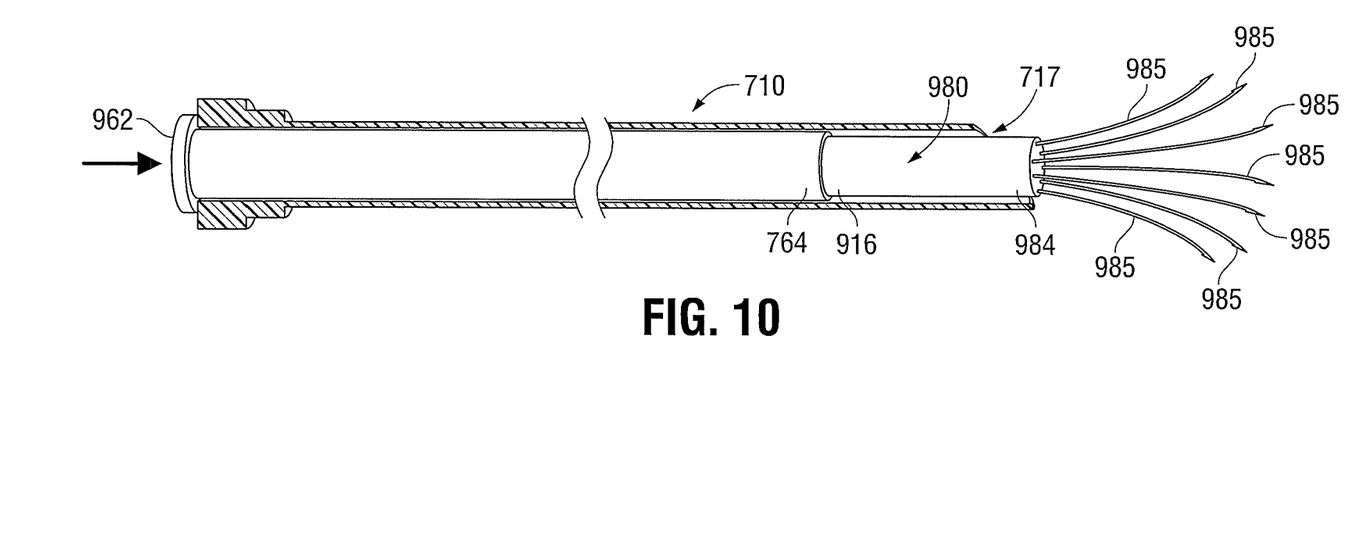
FIG. 10 is cross-sectional view of the drug eluting rod and the pusher rod shown in FIG. 9 disposed in association with the cannula assembly of FIG. 7, shown in a second configuration, in accordance with an embodiment of the present disclosure.

FIGS. 9 and 10 show a drug eluting rod 980 and a pusher rod 960 disposed, in part, within the passageway 711 of the cannula assembly 710 of FIG. 7. Drug eluting rod 980 includes a proximal end 916 and a distal end 984 having a plurality of barbed members 985 extending distally outwardly therefrom. The shape, size and number of barbed members 985 may be varied from the configuration depicted in FIGS. 9 and 10.

The pusher rod 960 includes a rod member 961 having a distal end 764, e.g., configured to engage the proximal end 916 of the drug eluting rod 980. In some embodiments, as shown in FIGS. 9 and 10, pusher rod 960 includes an end cap 962, e.g., configured to engage the cannula housing 731 (FIG. 7) of the cannula assembly 710. In some embodiments, the end cap 962 is configured to engage the cannula housing 731 for the purpose of limiting the axial translation of the rod member 961 within the passageway 711 of the cannula assembly 710, e.g., to position the drug eluting rod 980 within tissue (not shown).

A variety of drug agents may be delivered by devices according to embodiments of the present disclosure. Some examples of drug agents which may be delivered by devices according to embodiments of the present disclosure include chemotherapeutic agents such as without limitation cisplatin, paclitaxel, doxorubicin, fluorouracil, as well as other compounds such as without limitation prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropaniide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofluorophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-oc-hydroxyprogesterone acetate, 19-nor-progesterone, norgestrel, norethindrone, norethisterone, norethiederone, progesterone, norgesterone, norethynodrel, aspirin, indornethacin, naproxen, fenoprofen, sulindac, indoprofen, nitroglycerin, isosorbide dinitrate, propranolol, timolol, atenolol, aiprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, mitrinone, capropril, mandol, quanbenz, hydrochlorothiazide, ranitidine, flurbiprofen, fenufen, fluprofen, tolmetin, alciofenac, mefenamic, flufenamic, difiuinal, nimodipine, nitrendipine, nisoldipine, nicardipine, felodipine, lidoflazine, tiapamil, gallopamul, amlodipine, mioflazine, lisinoipril, enalapril, enalaprilat, captopril, ramipril, famotidine, nizatidine, sucralfate, etintidine, tetratolol, minoxidil, chlordazepoxide, diazepam, amitriptyline, and imipramine; opioids such as meperidine, hydrocodone, oxycodone, and semi-synthetic opioids such as oxymorphone, hydromorphone, opiates such as morphine and codeine, opioid antagonists such as without limitation naltrexone, nalbuphine, naloxone as well as opioid agonist/ antagonist compounds such as buprenorphine, and synthetic analgesics such as methadone, tramadol, fentanyl and sufentanil.

Some other examples of drug agents which may be delivered by devices according to embodiments of the present disclosure include vitamin and supplements such as vitamins B-12 (cyanocobalamin) and D2, anti-virals such as without limitation acyclorvir and zidovudine; proteins and peptides such as without limitation insulin, colchicine, glucagon, thyroid stimulating hormone, parathyroid and pituitary hormones, calcitonin, renin, prolactin, corticotrdphin, thyrotropic hormone, follicle stimulating hormone, chorionic gonadotropin, gonadotropin releasing hormone, bovine somatotropin, porcine somatotropin, oxytocin, vasopressin, GRE, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagulation factors, human pancreas hormone releasing factor, analogs and derivatives of these compounds, and pharmaceutically acceptable salts of these compounds, or their analogs or derivatives. On the molecular level, the various forms of the beneficial agent may include uncharged molecules, molecular complexes, and pharmaceutically acceptable acid addition and base addition salts such as hydrochlorides, hydrobromides, acetate, sulfate, laurylate, oleate, and salicylate. Examples of acidic compounds which may be delivered by devices according to embodiments of the present disclosure include salts of metals, amines or organic cations. Derivatives such as esters, ethers and amides may also be used.

A drug agent for delivery by devices according to embodiments of the present disclosure may be used alone or mixed with other agents. A drug agent for delivery by the presently-disclosed devices may include pharmaceutically acceptable excipients, polymeric carriers and/or additional ingredients, such as antioxidants, stabilizing agents, permeation enhancers, polysaccharides, proteins, nucleotides like aptamers, and fatty acids, etc., and fabricated into different forms, such as solution, suspension, gel, colloidal dispersion like liposome, or micro- and nano-particles for controlled delivery of the drug agent. A drug agent for delivery by the presently-disclosed devices may include a thermo-sensitive metal depositor or any such compound that increases the sensitivity of the target tissue, e.g., tumor, to ablation.

A drug agent for delivery by the presently-disclosed devices may include a cryoablation agent, e.g., liquid nitrogen, and may prove complementary to thermal ablation that uses electrosurgical energy at RF or microwave frequencies.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A drug-delivery cannula assembly, comprising:
a cannula housing defining a plurality of proximal openings, a plurality of distal openings, and a side opening, each of the plurality of distal openings being longitudinally aligned with a respective one of the plurality of proximal openings, each of the distal openings disposed in an arrangement corresponding to an arrangement of a plurality of obturator shafts of an obturator assembly, the cannula housing including a seal element disposed within a proximal portion of the cannula housing, the cannula housing configured to receive an obturator shaft of the plurality of obturator shafts of the obturator assembly through a respective one of the plurality of proximal openings and the seal element;
a plurality of cannulae, each of the plurality of cannulae defining a longitudinal axis and a passageway aligned with the longitudinal axis, each of the plurality of cannulae including a proximal end coupled to the cannula housing at one of the plurality of distal openings, each of the plurality of cannulae configured to receive a respective obturator shaft of the plurality of obturator shafts of the obturator assembly through the passageway; and
a supply line coupled to the cannula housing at the side opening, wherein the cannula housing is configured to fluidly-couple each of the plurality of cannulae to a drug source for supplying drugs via the supply line to each of the plurality of cannulae.

2. The drug-delivery cannula assembly of claim 1, wherein the passageway of each of the plurality of cannulae is configured to slideably receive a respective obturator shaft of the plurality of obturator shafts of the obturator assembly.

3. The drug-delivery cannula assembly of claim 1, wherein the passageway of each of the plurality of cannulae is configured to permit introduction of at least one surgical instrument used in performing a surgical procedure.

4. The drug-delivery cannula assembly of claim 1, wherein the cannula housing is adapted to releaseably engage the plurality of cannulae.

5. A drug-delivery cannula assembly, comprising:
a cannula housing defining a plurality of proximal openings, a plurality of distal openings, and a side opening, each of the plurality of distal openings being longitudinally aligned with a respective one of the proximal openings, each of the distal openings disposed in an arrangement corresponding to an arrangement of a plurality of ablation probes of an ablation device, the cannula housing including a seal element disposed within a proximal portion of the cannula housing, the cannula housing configured to receive an ablation probe of the plurality of ablation probes of the ablation device through a respective one of the plurality of first proximal openings and the seal element;
a plurality of cannulae, each of the plurality of cannulae defining a longitudinal axis and a passageway aligned with the longitudinal axis, each of the plurality of cannulae including a proximal end coupled to the cannula housing at one of the plurality of distal openings, each of the plurality of cannulae configured to receive a respective ablation probe of the plurality of ablation probes of the ablation device through the passageway; and
a supply line coupled to the cannula housing at the side opening, wherein the cannula housing is configured to fluidly-couple each of the plurality of cannulae to a drug source for supplying drugs via the supply line to each of the plurality of cannulae.

* * * * *